United States Patent
Tran et al.

(10) Patent No.: US 12,029,863 B2
(45) Date of Patent: Jul. 9, 2024

(54) INTRAVASCULAR TREATMENT SITE ACCESS

(71) Applicant: MicroVention, Inc., Aliso Viejo, CA (US)

(72) Inventors: Michelle Tran, Fountain Valley, CA (US); Tetsu Sumida, Irvine, CA (US); Mayank Goyal, Calgary (CA); Joseph A. Gulachenski, Trabuco Canyon, CA (US)

(73) Assignee: MicroVention, Inc., Aliso Viejo, CA (US)

(*) Notice: Subject to any disclaimer, the term of this patent is extended or adjusted under 35 U.S.C. 154(b) by 573 days.

(21) Appl. No.: 16/870,603

(22) Filed: May 8, 2020

(65) Prior Publication Data
US 2020/0269012 A1 Aug. 27, 2020

Related U.S. Application Data (63) Continuation of application No. 15/430,402, filed on Feb. 10, 2017, now Pat. No. 10,682,493.

(Continued)

(51) Int. Cl.
*A61M 25/00* (2006.01)
*A61B 17/221* (2006.01)
(Continued)

(52) U.S. Cl.
CPC ....... *A61M 25/0041* (2013.01); *A61B 17/221* (2013.01); *A61M 25/0023* (2013.01);
(Continued)

(58) Field of Classification Search
CPC ...... A61M 2025/0042; A61M 25/0023; A61M 25/0067; A61M 25/0068; A61M 25/00;
(Continued)

(56) References Cited

U.S. PATENT DOCUMENTS 4,571,240 A * 2/1986 Samson ............ A61M 25/0108
604/529
4,588,395 A * 5/1986 Lemelson ......... A61M 37/0069
604/218
(Continued)

FOREIGN PATENT DOCUMENTS

CN 104470576 A 3/2015
CN 109069796 A 12/2018
(Continued)

OTHER PUBLICATIONS

Australian Patent Office, Examination Report dated Jan. 20, 2021 in Australian Patent Application No. 2017217879, 4 pages.
(Continued)

*Primary Examiner* — Nilay J Shah
(74) *Attorney, Agent, or Firm* — Inskeep IP Group, Inc.

(57) ABSTRACT

The embodiments presented herein relate to concepts designed to eliminate the gap between a catheter and guide wire that can otherwise contribute to a catheter getting stuck within the vasculature. In an example embodiment, a microcatheter with an enlarged distal section is described. The enlarged portion of the microcatheter may be located close to the inner diameter of the guide catheter in order to reduce any open space between the microcatheter and the guide catheter, and the guidewire can be placed through the microcatheter and used to guide the system. The microcatheter can include one or more marker bands to aid in aligning the microcatheter correctly relative to the guide catheter. After the guide catheter and microcatheter are tracked to the appropriate treatment site, the microcatheter can then be used to deploy various medical devices to treat a patient.

23 Claims, 4 Drawing Sheets

Related U.S. Application Data (60) Provisional application No. 62/293,522, filed on Feb. 10, 2016.

(51) Int. Cl.
  *A61M 25/06* (2006.01)
  *A61M 25/09* (2006.01)
  *A61B 17/22* (2006.01)
  *A61M 25/01* (2006.01)

(52) U.S. Cl.
  CPC .... *A61M 25/0045* (2013.01); *A61M 25/0662* (2013.01); *A61M 25/09* (2013.01); *A61M 25/09016* (2013.01); *A61B 2017/22044* (2013.01); *A61B 2017/2212* (2013.01); *A61B 2017/2215* (2013.01); *A61M 2025/0042* (2013.01); *A61M 2025/0046* (2013.01); *A61M 25/0068* (2013.01); *A61M 25/0108* (2013.01); *A61M 2025/0183* (2013.01); *A61M 2025/0681* (2013.01); *A61M 25/09041* (2013.01); *A61M 25/0905* (2013.01); *A61M 2025/09116* (2013.01); *A61M 2025/09166* (2013.01); *A61M 2025/09175* (2013.01); *A61M 2205/0266* (2013.01)

(58) Field of Classification Search
  CPC .......... A61M 25/0041; A61M 25/0043; A61M 25/0108; A61M 2037/0007
  See application file for complete search history.

(56) References Cited

U.S. PATENT DOCUMENTS

| | | | |
|---|---|---|---|
| 4,719,924 A | 1/1988 | Crittenden et al. | |
| 4,976,703 A * | 12/1990 | Franetzki | A61M 25/0068 |
| | | | 604/523 |
| 4,991,602 A | 2/1991 | Amplatz et al. | |
| 5,069,673 A * | 12/1991 | Shwab | A61M 25/0023 |
| | | | 604/526 |
| 5,411,033 A | 5/1995 | Viera | |
| 5,449,362 A * | 9/1995 | Chaisson | A61M 25/104 |
| | | | 604/528 |
| 5,538,512 A * | 7/1996 | Zenzon | A61M 25/0125 |
| | | | 604/93.01 |
| 5,578,006 A * | 11/1996 | Schon | A61M 25/0068 |
| | | | 604/93.01 |
| 5,688,246 A * | 11/1997 | Waitz | A61M 25/0606 |
| | | | 604/164.11 |
| 5,860,963 A * | 1/1999 | Azam | A61M 25/0045 |
| | | | 604/528 |
| 6,059,748 A * | 5/2000 | Teirstein | A61M 25/0169 |
| | | | 604/510 |
| 6,537,480 B1 | 3/2003 | Becker et al. | |
| 6,669,652 B2 | 3/2003 | Becker et al. | |
| 6,761,708 B1 | 7/2004 | Chiu et al. | |
| 8,404,165 B2 | 3/2013 | Weber et al. | |
| 9,211,132 B2 | 12/2015 | Bowman | |
| 2002/0087076 A1* | 7/2002 | Meguro | A61M 25/0021 |
| | | | 600/433 |
| 2006/0144408 A1* | 7/2006 | Ferry | A61M 25/0054 |
| | | | 600/431 |
| 2009/0312745 A1 | 12/2009 | Goldfarb et al. | |
| 2010/0030113 A1 | 2/2010 | Morriss et al. | |
| 2010/0160899 A1* | 6/2010 | Gulachenski | A61M 25/0009 |
| | | | 604/525 |
| 2013/0190801 A1 | 7/2013 | Divino et al. | |
| 2014/0180246 A1 | 6/2014 | Comerota et al. | |
| 2015/0112256 A1* | 4/2015 | Byrne | A61M 25/1029 |
| | | | 604/103.02 |
| 2016/0022964 A1 | 1/2016 | Goyal | |
| 2016/0346503 A1 | 12/2016 | Jackson et al. | |
| 2016/0346507 A1 | 12/2016 | Jackson et al. | |
| 2017/0224953 A1 | 8/2017 | Tran et al. | |

FOREIGN PATENT DOCUMENTS

| | | | | |
|---|---|---|---|---|
| DE | 3820213 A * | 7/1989 | ........... | A61L 29/046 |
| DE | 4208912 C1 * | 5/1993 | ........ | A61M 25/0068 |
| EP | 3413963 A1 | 12/2018 | | |
| JP | 2007-520275 A | 7/2007 | | |
| JP | 2013-017835 A | 1/2013 | | |
| WO | WO-9529722 A1 * | 11/1995 | ........... | A61L 29/085 |
| WO | WO 2005/070475 A1 | 8/2005 | | |
| WO | WO 2007/039902 A2 | 4/2007 | | |
| WO | WO 2016/196177 A1 | 12/2016 | | |

OTHER PUBLICATIONS

Chinese Patent Office, Office Action dated Jul. 13, 2020 with English translation in Chinese Patent Application No. 201780022669. 2, 12 pages.
European Patent Office, Extended European Search Report dated Aug. 21, 2019 in European Patent Application No. 17750911.4, 8 pages.
WIPO, U.S. International Search Authority, International Search Report and Written Opinion dated Apr. 21, 2017 in International Patent Application No. PCT/US2017/017551, 8 pages.
Japan Patent Office, Office Action dated Feb. 21, 2023 with English translation in Japanese Patent Application No. JP2022-026471, 7 pages.
IP Australia, Examination Report dated May 17, 2023 in Australian Patent Application No. 2021257925, 4 pages.

\* cited by examiner

INTRAVASCULAR TREATMENT SITE ACCESS

RELATED APPLICATIONS

This application is a continuation of and claims priority to U.S. patent application Ser. No. 15/430,402 filed Feb. 10, 2017 entitled Intravascular Treatment Site Access, which claims benefit of and priority to U.S. Provisional Application Ser. No. 62/293,522 filed Feb. 10, 2016 entitled Intravascular Treatment Site Access, both of which are hereby incorporated herein by reference in their entireties.

BACKGROUND OF THE INVENTION

Guidewires are typically used in interventional procedures to access treatment areas. Guide catheters are typically slid over the guidewire to access the target area and act as a conduit for subsequently deployed microcatheters and/or therapeutic/treatment devices.

The vasculature can be particularly winding or tortuous, especially in the neurovasculature where small, tortuous blood vessels abound, making accessing the target area and delivering treatment devices particularly difficult. In a phenomenon known as the ledge effect, there is a gap between the guidewire and the distal end of the guide catheter which can get caught along blood vessel bifurcations, preventing the catheter from effectively tracking through the vasculature. The ophthalmic artery is just one region where there is a bifurcation, as well as significant tortuosity of the blood vessel, and is just one of many regions where the catheter can get stuck.

A system which would minimize or eliminate the gap between the guidewire and guide catheter is desirable to prevent the catheter from getting stuck in the vasculature.

SUMMARY OF THE INVENTION

In one embodiment, a microcatheter with an enlarged distal section is described. The enlarged portion of the microcatheter is located close to the inner diameter of the guide catheter in order to reduce any open space between the microcatheter and the guide catheter, and the guidewire can be placed through the microcatheter and used to guide the system. The microcatheter can include one or more marker bands to aid in aligning the microcatheter correctly relative to the guide catheter. After the guide catheter and microcatheter are tracked to the appropriate treatment site, the microcatheter can then be used to deploy various medical devices to treat a patient.

In one embodiment, a microcatheter with an enlarged distal section includes multiple marker bands to aid in visualization. The marker bands can be used to align the microcatheter appropriately relative to the guide catheter so that the microcatheter enlarged distal section coincides with the guide catheter distal tip. The guidewire is used to access a treatment site and the microcatheter and guide catheter can be tracked over the guidewire.

In one embodiment, an obstruction removal system is described. The obstruction removal system includes a guide catheter, a microcatheter with an enlarged distal section delivered through the guide catheter, and an obstruction removal device delivered through the microcatheter. A guidewire is tracked through the microcatheter and the guidewire is used to help track the microcatheter and guide catheter near the treatment site. Once the treatment site is accessed, the microcatheter can be used to deliver an obstruction removal device, such as a clot retrieval device (e.g., a stentriever), in order to remove an obstruction (e.g., a clot).

In one embodiment, a guidewire is described. The guidewire includes a projection to minimize or eliminate the gap between the guidewire and the guide catheter. In one embodiment, the projection is bulbous. The projection can further include a radiopaque marker to aid in imaging and placement of the guidewire.

In one embodiment, the guidewire includes a shapeable or malleable distal tip and a torque device. The shapeable or malleable distal tip can be bent in a particular direction, and the torque device clamps down on the guidewire to keep it fixed. The guidewire can then be rotated in a particular direction so that the distal tip lines up with a particular blood vessel in order to aid in tracking the guidewire through the vasculature.

In one embodiment, a method of using a guidewire is described. The guidewire includes a distal projection and a radiopaque marker. A guide catheter also includes a radiopaque marker. The guidewire is retracted or the guide catheter is pushed so that the guidewire projection contacts the guide catheter. The guidewire and guide catheter can then be advanced together by pushing the guide catheter. The guide catheter radiopaque marker and guidewire radiopaque marker either sit flush or next to each other, and the user can tell due to the augmented radiopacity when viewed by traditional imaging systems. The user can optionally use a torquer to lock and rotate the guidewire so that the distal tip is directed in a particular direction to aid in navigating the guidewire through the vasculature.

In one embodiment, a rapid exchange system is described. The rapid exchange system minimizes the gap between the guidewire and the guide catheter in scenarios where the catheter can be caught at vessel bifurcations, the rapid exchange system would track over the guidewire and includes a distal enlarged section to bridge the gap between the guidewire and the guide catheter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Many interventional procedures utilize a guide catheter, also known as a distal-access catheter (DAC), to access the vicinity of a treatment site. A thin, flexible guidewire is tracked through the vasculature and the guide catheter/DAC is tracked over this guidewire to access the treatment site. Once the region is accessed, a microcatheter is placed through the guide catheter and the guidewire is withdrawn. The microcatheter is then used to deliver to help deliver a therapeutic or treatment agent, for example a stent, clot retrieval device, or coils used to fill an aneurysm. Guide catheters typically have a relatively large diameter since they must accommodate both a guidewire and a microcatheter. Tracking a guide catheter through the vasculature can be difficult due to the tortuous nature of the anatomy, especially in the brain or neurovasculature where the vessels can be small and tortuous and branch vessels abound making it difficult to track a catheter to the proper treatment site.

Figure 1:
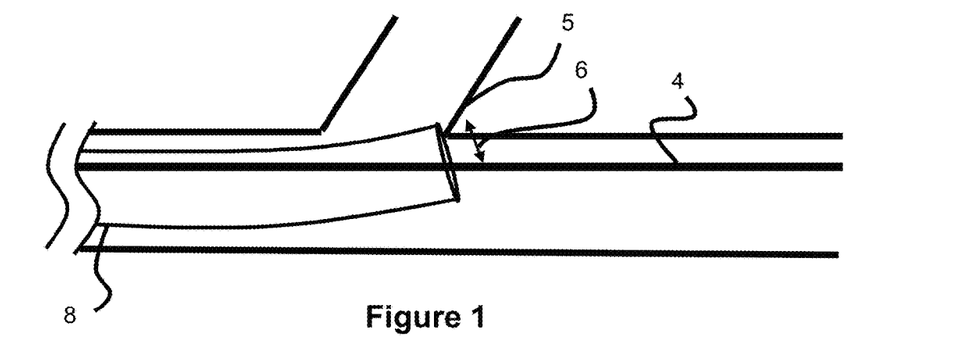
FIG. 1 illustrates a traditional guide catheter getting stuck at a vessel bifurcation, a phenomenon known as the ledge effect.

Vessel bifurcations present a navigational obstacle due to a gap between the guidewire and the distal end of the guide catheter which can become stuck at the bifurcation. This phenomenon is known as the ledge effect, and is shown in FIG. 1 in which a gap 6 between guidewire 4 and guide catheter 8 gets caught at a vessel bifurcation 5. In one example, a typical guide catheter 8 can have an inner diameter of 0.07" while a guidewire 4 can have a diameter ranging from 0.014"–0.035". The gap size 6 (defined as the radius of the guide catheter 8 minus the radius of the guidewire 4) will typically be between 0.0175"-0.028". This gap size 4 corresponds to between 25-40% of the overall guide catheter inner diameter, which represents a significant amount of open space. Problems with guide catheter tracking can delay treatment or even make treatment impossible increasing the risk to the patient. The following embodiments address this issue.

US2016/0022964 entitled "System and methods for intracranial vessel access" to Goyal, discloses a guidewire based system to treat the ledge effect complication with a guidewire having an enlarged region designed to bridge the gap between the overlying guide catheter and the underlying guidewire. US2016/0022964 is hereby incorporated by reference in its entirety.

Figure 2:
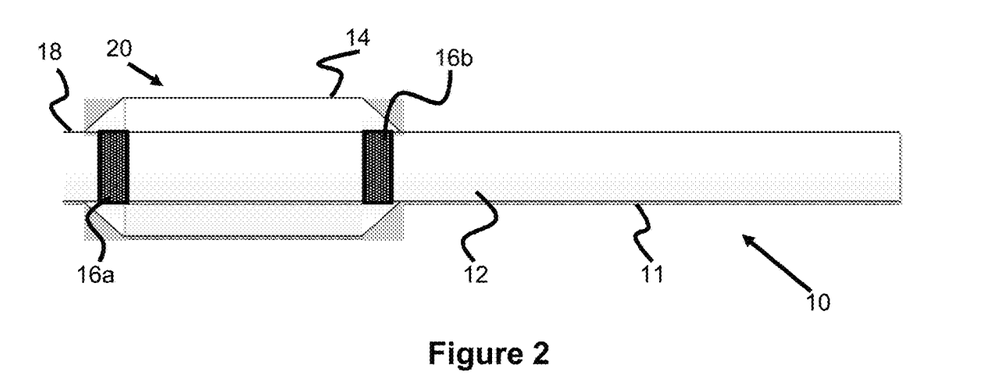
FIGS. 2-3 illustrate a microcatheter with an enlarged distal section according to one embodiment, where the microcatheter can be used to address the ledge effect issue.
Figure 3:
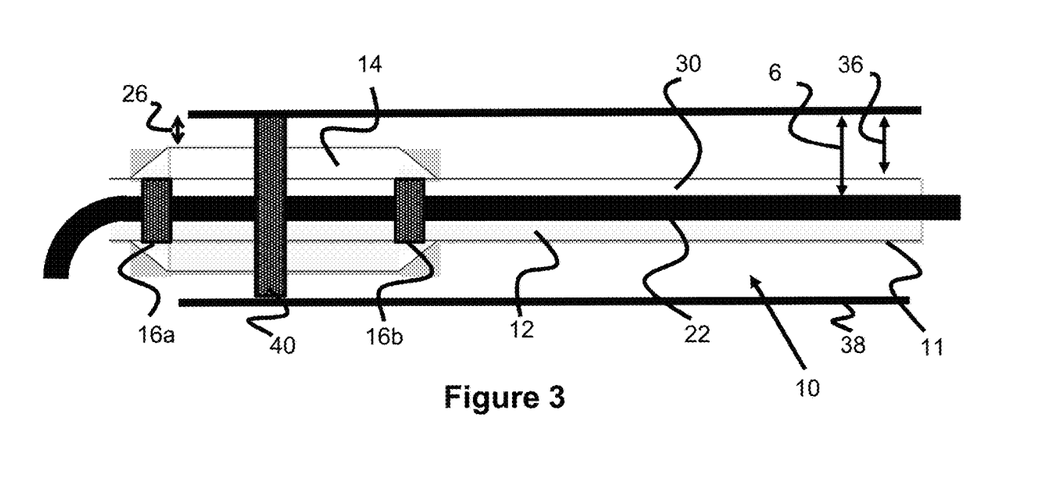

FIGS. 2-3 and the following disclosure relate to an intermediate microcatheter 10 that has an enlarged region 14 that minimizes any gap between the guidewire 22 and the overlying outer guide catheter 38. In other words, the intermediate microcatheter 10 slides over the guidewire 22 and its enlarged distal end 14 takes up the open space within the lumen of outer guide catheter 38. When the enlarged region 14 is positioned at or somewhat beyond the distal end of the outer guide catheter 38, the "ledge" created by outer guide catheter 38 is diminished or eliminated, thereby avoiding being caught up at vessel bifurcations and other vessel shapes. Additionally, several later embodiments in this specification (see FIGS. 4-9) disclose improved guidewire-based systems in which the guidewire has an enlarged region that bridges the gap between the overlying guide catheter and the guidewire.

FIG. 2 illustrates a microcatheter 10 with a bulbous or enlarged distal section 14. The bulbous/enlarged distal section 14 can have a generally cylindrical shape with tapered ends, a longitudinally rounded shape, or any other common shapes. Though distal section 14 is enlarged, the inner diameter defining the inner lumen 12 of microcatheter 10 is preferably consistent throughout the length of microcatheter 10. Preferably the bulbous or enlarged distal section 14 of microcatheter 10 exactly matches up with or is slightly smaller than the inner diameter of the overlying guide catheter 38. As seen in FIG. 3, this close fit of the enlarged distal section 14 bridges or fills the gap between the intermediate microcatheter 10 and guide catheter 38, creating a snug interface between the two catheters to prevent any open exposed surface which could otherwise get caught at a vessel bifurcation. For example, the inner diameter of the outer guide catheter 38 is about 0.070 inch, while the diameter of the enlarged distal section 14 is about 0.067 inch. This reduces the gap size 26 to about 0.0015 inch on all sides, as opposed to a gap size 6 between the guidewire 22 and the outer guide catheter 38 of about 0.0175-0.028 inch on all sides (with a 0.014-0.035 inch guidewire). A gap size of 0.0015" represents only about 2% of the total inner diameter of the outer guide catheter 38. In other examples, the enlarged distal section 14 has a diameter that is almost the same diameter as the inner diameter of the guide catheter 38. In either of these two examples, the diameter of the enlarged distal section 14 is close to the inner diameter of the outer guide catheter 38 and the limited open space does not provide enough room for a vessel to get caught. Bulbed/enlarged section 14 may have a linear taper 20 as shown in FIG. 2, or the taper may be rounded or elliptical in shape. The distal tip 18 of the intermediate microcatheter 10 preferably maintains an inner diameter size that is generally uniform of the proximal portions of the intermediate catheter 10 (i.e., a relatively close fit with the guidewire 22) in order to minimize the gap between the inner diameter of microcatheter 10 and guidewire 22.

In an alternative embodiment, the inner diameter of the lumen of the microcatheter 10 is larger within the enlarged region 14. However, in this embodiment it would be desirable that the distal tip 18 of microcatheter 10 has a comparatively reduced inner diameter to eliminate any large gap between guidewire 22 and the intermediate microcatheter 10 in order to prevent any open, catching surfaces between the blood vessel and microcatheter 10.

Distal marker band 16a and proximal marker band 16b are located on the microcatheter body 11 at the distal and proximal ends of the enlarged distal section 14, respectively, to aid in visualizing the position of intermediate microcatheter 10 and, in particular, the distal section of microcatheter 10. In one embodiment, a third marker band (not shown) could be placed at the distal tip 18 of the intermediate microcatheter 10, beyond the enlarged distal section 14, such that the distal tip 18 of the device is viewable within a patient.

In one illustrative example of a bulbed intermediate microcatheter 10 of the present invention, the outer guide catheter 38 has an inner diameter of about 0.07", the enlarged distal section 14 of the intermediate microcatheter 10 has an outer diameter of about 0.067", the area of the microcatheter body 11 proximal of the enlarged section 14 has an outer diameter of about 0.033", while the distal tip 18 has an outer diameter of about 0.031". A smaller outer diameter of the distal tip 18 will promote increased flexibility and trackability, while a larger outer diameter of the proximal section of the microcatheter body 11 will promote greater push strength. The inner diameter of intermediate microcatheter 10 is constant at about 0.021". These dimensions can also vary based on which guidewire or guide catheter is used. For example, the outer diameter of the intermediate microcatheter 10 can range from about 0.013" to about 0.073", the length of the enlarged section 14 length is about 0.5 cm to about 3 cm, and the distal tip 18 has a length between about 0.5 cm to about 6 cm. The inner diameter of the intermediate microcatheter 10 is consistent throughout its length at about 0.01 inches to about 0.045 inches. The working length of the intermediate microcatheter 10 is about 148-168 cm. A lubricious coating can optionally be used over the enlarged section 14 of the intermediate microcatheter 10.

The intermediate microcatheter 10 can be manufactured in a variety of ways. In one example, the inner liner of intermediate microcatheter 10 is comprised of PTFE, LDPE, LLDPE, or HDPE. A stainless steel coil is placed over the inner liner and is either a coiled wire or flat wound wire of about 0.00075 inches to about 0.0015 inches. A stainless steel flat wire or braid is placed over the coil. An outer shaft layer can be placed over the reinforcement, this outer layer can comprise different durometers and different types and amounts of material, for example ranging in shore hardness from 10A to 72D. Generally, it is desirable to have more stiffness at the proximal end and more flexibility at the distal end, so the outer layer proximal section would generally comprise stiffer material than the outer layer distal section. One or two platinum/iridium (90%/10%) marker bands are placed under the bulb for visualization, with an additional marker band placed at the distal tip 18 of intermediate microcatheter 10. The enlarged outer diameter region 14 comprising the bulb is comprised of a relatively soft polymeric material such as polyblend 18A, 30A, a balloon, or any Shore Hardness A durometer material, this softness will aid flexibility as well as navigation through a guide catheter 38 in scenarios where the inner diameter of outer guide catheter 38 matches closely with the bulbed section 14 outer diameter, or scenarios where bulbed section 14 contacts a portion of the vessel and the soft material helps prevent vessel trauma (e.g., at a blood vessel bifurcation).

Microcatheter 10 can utilize a lubricious coating along its entire length, or selectively along particular portions to augment tracking ability of the microcatheter. A lubricious coating would be particularly useful in the bulbed region 14 of microcatheter 10 since this is the largest cross-sectional portion of the microcatheter 10, and is also the part of the microcatheter which is most likely to contact overlying guide catheter 38. In one example, the lubricious coating is hydrophilic and can utilize multiple layers—for instance, a well-adhering basecoat layer formed from a crosslinker and a highly lubricious topcoat layer chemically adhered to the basecoat layer.

Guide catheters 38 typically utilize a marker band 40 located approximately 3 cm from its distal tip so the user can visualize the distal tip within a patient (illustrated in FIG. 3). The user would track microcatheter 10 through guide catheter 38 so that the bulbed/enlarged region 14 of intermediate microcatheter 10 is located flush with the distal tip of the outer guide catheter 38, as shown in FIG. 3. This will ensure that there is no gap or a minimized gap between guide catheter 38 and microcatheter 10. This minimized gap is shown as element 26 whereas the proximal gap 36 reflects the gap between guide catheter 38 and the reduced proximal portion of microcatheter 10. Proximal gap 36 can be thought of as the normal gap between a microcatheter and guide catheter in scenarios where a typical microcatheter rather than a bulbed microcatheter was used. Gap 6, as discussed earlier, represents the typical gap that is present between a guidewire 22 and a guide catheter 38 in the typical procedure where the guide catheter is directly tracked over the guidewire.

Bulbed intermediate microcatheter 10 acts as an intermediary between guidewire 22 and guide catheter 38 as previously described. When intermediate microcatheter 10 is appropriately placed as shown in FIG. 3, the user will see a line of marker bands—the microcatheter distal marker band 16a, the outer guide catheter 3 cm marker band 40, and the proximal marker band 16b. Each of these marker bands can be either a series of discrete segments (one for each marker band) with gaps in between, or one elongated and continuous segment. This line of marker bands ensures proper alignment so the user can tell that the enlarged distal section of microcatheter 10 is past the distal tip of guide catheter 38, such that the enlarged section 14 of microcatheter 10 occupies the space within guide catheter 38. Once the user can confirm this, the user can proceed to track the guidewire, the intermediate microcatheter over the guidewire, and the guide catheter over the intermediate microcatheter.

Since the intermediate microcatheter 10 is used as a bridging device between guidewire 22 and guide catheter 38, there will also be a minor gap 30 present between guidewire 22 and microcatheter 10. It is desirable that this gap 30 is not eliminated entirely to avoid friction between the guidewire 22 and the intermediate microcatheter 10. However, this gap 30 is relatively small and therefore a vessel bifurcation will likely not get caught. In one example, microcatheter 10 has a consistent inner diameter of about 0.021" which would accommodate a guidewire 22 sized from 0.014" to 0.018". Applying the earlier formula which defined the gap size as the radius of the outer element (here, microcatheter 10) minus the radius of the inner element (here, guidewire 22), this results in a gap size between the microcatheter and guidewire of about 0.00205" to about 0.0035". If a microcatheter were not used at all, as discussed earlier, the gap size could range from about 0.0175"-0.028"—in other words, the gap size is reduced to about 7-20% of its initial value simply by using a microcatheter. Using a bulbous microcatheter, as discussed earlier, will further reduce the gap between the microcatheter and the overlying guide catheter. Thus, the advantage of using a bulbed microcatheter 10 as an intermediate element between the guidewire 22 and guide catheter 38 is two-fold: 1) it minimizes the gap that is normally present between the guidewire and the guide catheter and 2) the presence of the bulbed/enlarged section 14 of microcatheter 10 minimizes the gap between microcatheter 10 and guide catheter 38. Reducing or minimizing the gap in turn minimizes the amount of open space available for a blood vessel bifurcation to be caught, which in turn substantially enhances trackability of the device through the tortuous anatomy.

Alternative embodiments could utilize a bulbed intermediate microcatheter 10 with more or fewer marker bands. In one example, bulbed intermediate microcatheter 10 could use three marker bands where the third intermediate marker band would sit in between distal marker band 16a and proximal marker band 16b. This intermediate marker band would align with the guide catheter 3 cm distal tip marker 40. The presence of so many marker bands might make them individually difficult to see, and therefore such an embodiment would be best served for a larger microcatheter with an elongated enlarged region 14. In another example, intermediate microcatheter 10 could use one marker band where the microcatheter marker band would align with the guide catheter distal tip marker band 40 to ensure proper positioning of the intermediate microcatheter.

In one method of use, a guidewire 22 is tracked through a patient's vessel and the guide catheter 38 is tracked over the guidewire 22. When the guidewire 22 is navigated through a vessel bifurcation region, the user tracks the bulbed intermediate microcatheter 10 over the guidewire 22 so that the microcatheter 10 is located at the distal region of the guide catheter 38 and extend out of the distal tip of the guide catheter 38, such that the distal tip 18 of the intermediate microcatheter 10 is located distal of the outer guide catheter 38 and the enlarged region 14 of the intermediate microcatheter 10 bridges the gap between the guidewire 22 and the guide catheter 38. To achieve the desired position, the intermediate microcatheter 10 has 2 marker bands, 16a and 16b, as shown in FIGS. 2-3. The user manipulates the intermediate microcatheter 10 so that the two marker bands 16a and 16b are located on either side of guide catheter 3 cm distal tip marker band 40. The user tracks intermediate microcatheter 10 and guide catheter 38 together as a unit over the guidewire 22 by pushing both simultaneously through the bifurcation region.

In another embodiment, bulbed intermediate microcatheter 10 is used as part of an implant delivery system. Bulbed microcatheter 10 addresses the ledge effect issue, while also being used a conduit to deliver an implant, such a stent, clot retrieval device, or embolic coils. After the guidewire 22 is used to navigate intermediate microcatheter 10 to the treatment site, the guidewire 22 is withdrawn through intermediate microcatheter 10. The intermediate microcatheter 10 is subsequently used to deliver an implant.

In one embodiment, bulbed intermediate microcatheter 10 is part of a clot retrieval system. Clots can lead to issues such as ischemic stroke due to decreased bloodflow to areas distal of the clot. Clot retrieval devices are mechanical structures designed to grab, retain, and remove a clot from the vasculature. U.S. Pat. No. 9,211,132 entitled "Obstruction Removal System" discloses a clot retrieval device and is hereby incorporated by reference in its entirety. Stentrievers are one type of clot retrieval device which take the form of a unitary tubular wire mesh or cylindrical laser cut sheet element that are designed to retain a clot. U.S. Pat. Nos. 8,679,142, 8,357,179, 6,402,771 further disclose stentriever devices and are hereby incorporated by reference in their entirety.

In one embodiment bulbed intermediate microcatheter 10 is part of a clot retrieval system. In another embodiment, bulbed microcatheter 10 is used as part of a stentriever system. Bulbed intermediate microcatheter 10 addresses the ledge effect issue, where the system helps a clot retriever access a problematic region (e.g. a bifurcation region in the neurovasculature). The system includes a guide catheter 38, intermediate microcatheter 10, guidewire 22, and clot retriever or stentriever (not pictured). Guide catheter 38 is more structurally rigid than microcatheter 10 and would track through a majority of the vasculature to the general region of the delivery procedure. Intermediate microcatheter 10 is smaller than guide catheter 38, is delivered through the guide catheter, and accesses the actual treatment site thus providing a conduit to the treatment site. Guidewire 22 helps track microcatheter 10 and guide catheter 38 through the vasculature to access the treatment site. The delivery procedure is similar to the one described above where the microcatheter can be tracked over the guidewire and placed beyond the distal tip of the guide catheter to track the system through vascular bifurcation regions. When the system is appropriately placed, guidewire 22 is withdrawn through bulbed intermediate microcatheter 10 and microcatheter 10 is then used as a conduit for a clot retriever or a stentriever.

In one embodiment, the clot retrieval device or stentriever is pre-delivered through bulbed intermediate microcatheter 10 to a distal section of the intermediate microcatheter 10, such that the distal end of the clot retrieval device or stentriever is located either flush with the distal end of the intermediate microcatheter 10 or beyond the distal end of the intermediate microcatheter 10. Intermediate microcatheter 10 is housed within a guide catheter 38, similar to FIG. 3. The outward force provided by the clot retrieval device can be used to help navigate the catheters and stentriever through a vessel bifurcation region and through the tortuous anatomy; that is, the force provided against the microcatheter by the clot retrieval device can help direct the system in a particular direction at a vessel bifurcation, and can also held direct the system through the tortuous anatomy.

In some embodiments, the bulbed intermediate microcatheter 10 is used without the guidewire 22, being used for the tracking of the guide catheter 38 and then for the delivery device of subsequently delivered therapeutic materials. The distal section 14 of bulbed intermediate microcatheter 10 is preferably coated with a lubricious coating, and this coating would both decrease tracking friction through guide catheter 38 and also promote smooth tracking through the vasculature. Additionally, since the distal inner diameter of the bulbed intermediate microcatheter 10 is significantly smaller than the inner diameter of the outer guide catheter 38, there is less open lumen surface available for a vessel bifurcation to be caught.

In some embodiments, guidewire 22 is first deployed and bulbed microcatheter 10 is then tracked over the guidewire 22, while guide catheter 38 is separately tracked over the bulbed microcatheter 10. In some embodiments, guidewire 22 is first deployed, while bulbed microcatheter 10 and guide catheter 38 are deployed simultaneously, and together, over the guidewire.

Figure 4:
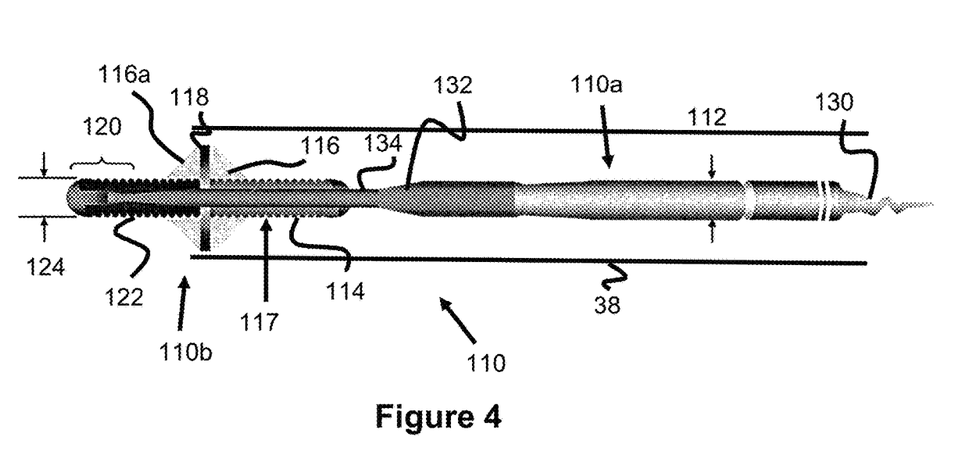
FIG. 4 illustrates a guidewire with a projection according to one embodiment.

Other contemplated embodiments used to address the ledge effect problem utilize a guidewire with an enlarged region that bridges the gap between the guidewire and guide catheter. For example, FIG. 4 shows a guidewire 110 having a radial projection 116 at its distal end to radially bridge a gap within a guide catheter 38. In this regard, an intermediate microcatheter with an enlarged distal end, as discussed in the previous embodiments, is unnecessary.

The radial projection 116 is located within the distal section 110b of the guidewire 110 and can have a number of shapes, including ellipsoid, oval, circular, bulbous, or diamond. Projection 116, in one particular example, has a bulbous shape. Projection 116 is preferably comprised of a soft-polymer material to enhance tracking through the patient's vessels. A soft-polymer is less stiff than a hard-polymer, and will be more malleable and less likely to jump or suddenly move when the radial projection 116 contacts a vessel wall. It is also preferable for projection 116 to slide rather than jump against the vessel wall in order to prevent any big, unexpected movements. The smooth transition formed by taper 116a on the projection 116 further prevents the guidewire 110 from jumping around after contacting the vessel wall within the vasculature.

Projection 116 further includes a radiopaque marker 118 that, in one example, is a circular marker band located around the polymeric radial projection 116. The marker band can comprise platinum, tantalum, palladium, gold, or any similar highly dense metallic elements, alloys, or compounds which would be visible via imaging techniques.

The distal section 110b of the guidewire 110 also includes a tapered section 132, a reduced diameter section 134, and a coil 117 which is located over the reduced diameter section 134. Coil 117 is comprised of two different coil elements; a first non-radiopaque coil portion 114 (in one example comprised of stainless steel), and a second radiopaque coil portion 122 useful for imaging and viewing the distal section of the catheter (in one example comprised of platinum). Coil 117 aids in flexibility and provides a soft contact surface to avoid vessel trauma if the guidewire tip hits a vessel wall.

Guidewire 110 also includes a shapeable distal tip 120 which can be shaped to aid in navigating the guidewire through the vasculature. A shaping mandrel can be used to help shape distal tip 120 of the guidewire 110 so that the distal tip bends in a particular direction. Guidewire shaping mandrels are currently used to pre-shape the distal tip of the guidewire. These shaping mandrels are typically packaged along with the guidewire, and the user uses the mandrels to impart a bent shape onto the distal tip of the guidewire prior to placing the guidewire within the patient's vasculature. The bent shape is useful to orient the guidewire to navigate the vasculature. The user can rotate the guidewire so the bent tip aligns with the direction the user wants the guidewire to go, such as at a vessel bifurcation point, thus aiding navigation of the guidewire and the catheter tracked over the guidewire through the tortuous anatomy.

Guidewire 110 is preferably tapered so that its proximal section 110a has a larger diameter than the distal section 110b. This tapered shape will aid in torque response, so that the torque generated by torqueing the proximal end of the system will easily carry through the guidewire 110 and result in a sufficient torque response at the distal tip 120 of guidewire 110. In one example, guidewire 110 has a proximal diameter 112 of about 0.013 inches to about 0.014 inches, and in a more specific example has a diameter of about 0.0135 inches. This diameter can be slightly tapered or can be substantially constant. Guidewire 110 has a distal section diameter 124 of about 0.012 inches. The distal section diameter 124 is directed only to the diameter of the distal coil 117 comprising coil elements 114 and 122.

Figure 5:
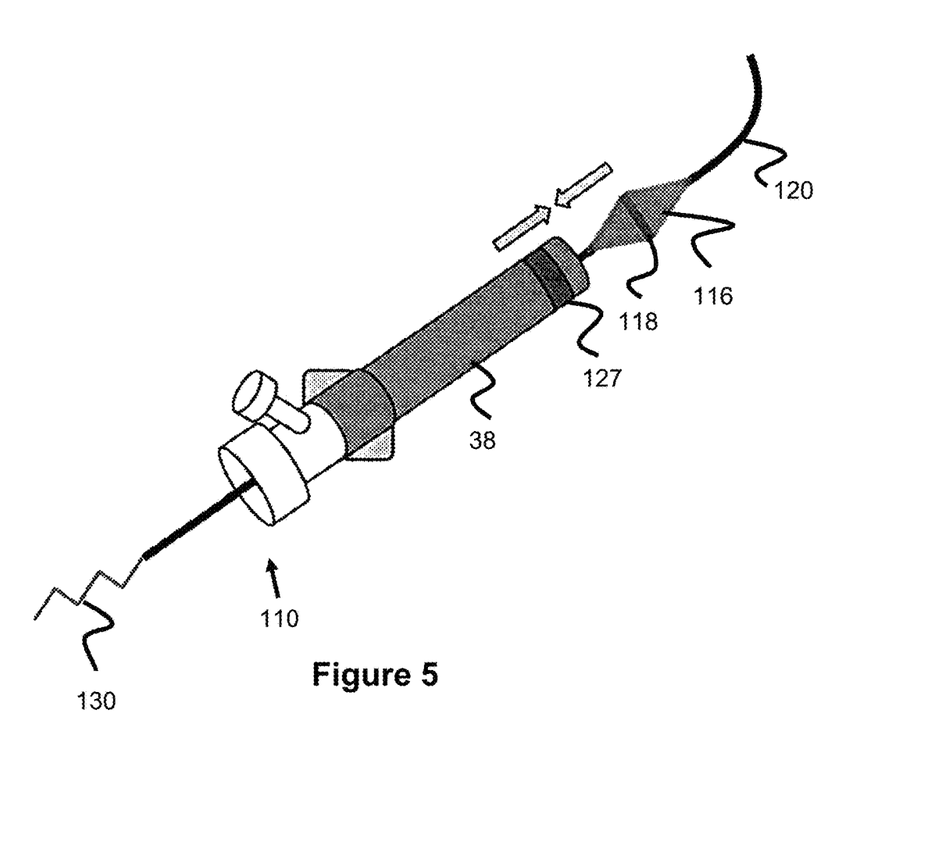
FIG. 5 illustrates a guidewire with a projection and a guide catheter according to one embodiment.
Figure 6:
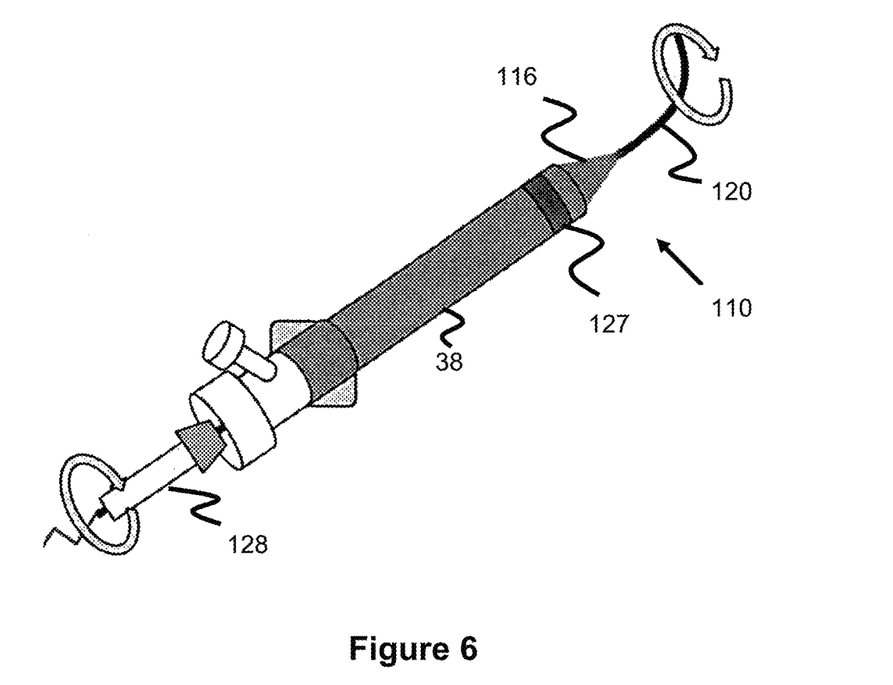
FIG. 6 illustrates a guidewire with a projection, a catheter, and a torquer used to manipulate the guidewire according to one embodiment.

FIGS. 4-6 show an optional docking element 130 which is located at the proximal part of the guidewire 110 and that serves as a proximal guidewire extension to provide a physician to better grip the guidewire 110 and therefore increase the ease of advancing, retracting, and torqueing the guidewire 110. In one example, docking element 130 is a proximal wire and guidewire 110 is built over a distal section of docking element 130, where docking element 130 ends within a proximal section of guidewire 110.

In one example, the proximal section 110a of guidewire 110 is comprised of a stainless steel core wire and the distal section 110b of guidewire 110 (including tapered section 132 and reduced diameter section 134) is comprised of a nitinol core wire.

In one example, guidewire 110 is about 200 centimeters. The stainless steel core wire comprising proximal section 110a extends for about 140 centimeters and the stainless steel core wire comprising distal section 110b extends for about 60 centimeters. The stainless steel coil 114 extends for about 37 centimeters while the platinum coil 122 covers about 3 centimeters. The shapeable length section 120 extends for about 1.4 centimeters. The hydrophilic coating on the distal section of guidewire 110 extends for about 140 centimeters (covering the distal part of the guidewire and extending until the distal tip of the guidewire).

FIGS. 5-6 show guidewire 110 from FIG. 4 along within a guide catheter 38. In FIG. 5, guidewire 110 illustrates projection 116 and radiopaque marker 118, while the distal part of guidewire 110 is located beyond the distal end of guide catheter 38. This configuration the guidewire is used to access the vicinity of a target treatment site, and guide catheter 38 is subsequently pushed or tracked over the guidewire 110.

In FIG. 6, guidewire 110 is either pulled back into guide catheter 38, or guide catheter 38 is pushed over guidewire 110 so that the projection 116 contacts and fits into guide catheter 38 (e.g., the projection 116 is undersized compared to the lumen of the guide catheter 38 or even slightly oversized but composed of a malleable material that can be deformed and withdrawn into the catheter 38). Alternatively, a push/pull combination technique can be used. If projection 116 has a bulbous shape, as shown in FIGS. 4-6, then guide catheter 38 should contact the area of projection 116 that has the largest diameter. Guide catheter 38 includes a radiopaque marker 127. The guidewire radiopaque marker 118 either is located flush with the guide catheter's radiopaque marker 127, or the guidewire radiopaque marker 118 is located just distal of guide catheter radiopaque marker 127. In any case, the presence of two radiopaque elements so close to each other will augment the imaging of the system when viewed by the user, so the user can tell that the two elements are aligned and that guidewire 110 is snug with guide catheter 38 and the system can be pushed through the vasculature.

When guidewire projection 116 contacts guide catheter 38, there is substantially no gap between guidewire 110 and guide catheter 38. This helps mitigate the ledge effect since there is substantially no gap or open surface for the vessel to snag onto. Normally, the presence of a gap creates a void where the guide catheter can get stuck. However, when the guidewire projection 116 is located snug with the guide catheter 38, there is no such gap and the projection slides against the vessel so that the guide catheter does not get stuck at the vessel bifurcation. As discussed earlier, the projection preferably comprises a soft polymer to promote a sliding effect when the projection contacts the vessel. Additional hydrophilic coating, additional lubricious coatings, or lubricious polymers can be used to further enable the projection to slide against the vessel wall.

The guidewire 110 of FIGS. 4-6 can be advanced in a few different ways. In a first method, guidewire 110 is deployed distal of guide catheter 126 and guide catheter 38 is pushed over guidewire 110. If guide catheter 38 gets stuck (for example, due to the ledge effect), guidewire 110 is retracted so that the guidewire projection 116 contacts guide catheter 38. Guide catheter 38 is then pushed forward, which advances both guidewire 110 and guide catheter 38 as a unit. Guidewire 110 also advances as guide catheter 38 advances since the guide projection 116 contacts the guide catheter 38. In a second method, the user places the guidewire projection 116 at the distal section of the guide catheter 38, and guidewire 110 and guide catheter 38 are pushed together as a unit through the vasculature. Once guide catheter 38 is appropriately placed, a microcatheter can be tracked through the guide catheter and the guidewire 110 is withdrawn, and the microcatheter can be used to deliver a therapeutic agent (e.g. stents, coils, clot retrieval devices), or alternatively the guide catheter 38 itself can be used to deliver a therapeutic agent.

As discussed earlier with regard to the bulbed microcatheter 10 embodiments, small gaps may be allowable as long as they are too small for the vessel bifurcation to get caught therein—therefore, some embodiments may utilize a small gap between guidewire projection 116 and guide catheter 38 such that the projection 116 does not necessarily contact the guide catheter 38.

FIG. 6 shows a torquer 128 used to lock and torque guidewire 110. The torquer 128 includes a compressible collet that pushes down on and lock the guidewire 110. The torquer 128 can be twisted or rotated to compress the collet to lock the guidewire 110, or torquer 128 can contain a movable element linked to the collet to lock guidewire 110 via the collet. In FIG. 6, the torquer 128 is shown being applied to a proximal section of guidewire 110. Torquer 128 is used to lock on to the guidewire 110 so the guidewire distal tip 120 is in a fixed position relative to the torquer 128. The user would lock the guidewire 110 and then push the guidewire 110 through the vasculature. Since guidewire 110 is locked in a certain position via torquer 128, the direction of the bent distal tip 120 will not change unless torquer 128 is rotated. Torquer 128 allows the guidewire orientation to be locked and prevents accidental rotation of guidewire 110 while the guidewire 110 is pushed to advance said guidewire through the vasculature. When the user is stuck at a bifurcation and wants to reorient guidewire 110, the user can then rotate torquer 128 which rotates the guidewire 110 to change the orientation of the guidewire distal tip 120 so that its aligned in another direction.

In other embodiments, the guidewire projection 116 can selectively lock to guide catheter 38. In one example, the projection 116 can include threaded elements which thread into a corresponding groove in the guide catheter 38 so the two elements can be locked together similar to a screw. In another example, the projection 116 can include an enlarged ring which mates with a corresponding recess in guide catheter 38. In another example, guidewire projection 116 includes a recess and the guide catheter 38 includes a projecting ring which mates with said recess. The mating can be done by force, where if the user applies enough force the elements will mate (to lock) and un-mate (to unlock) relative to each other. In one example, a torquer similar to the one described above can be used to lock the guidewire 110 to the guide catheter 38 when the two elements are in contact with each other or mated to each other.

The earlier description discussed advantages of a soft polymer used for guidewire projection 116, where one advantage is that the material properties of the soft polymer would promote a sliding contact interface between guidewire projection 116 and the blood vessel. One further advantage of a soft polymer used for the projection is malleability. When guidewire 116 is withdrawn, the user can retract guidewire 116 through the guide catheter 38. The malleability of a soft polymer will enable the guidewire projection 116 to compress and be retracted through guide catheter 38 with ease.

Figure 8:
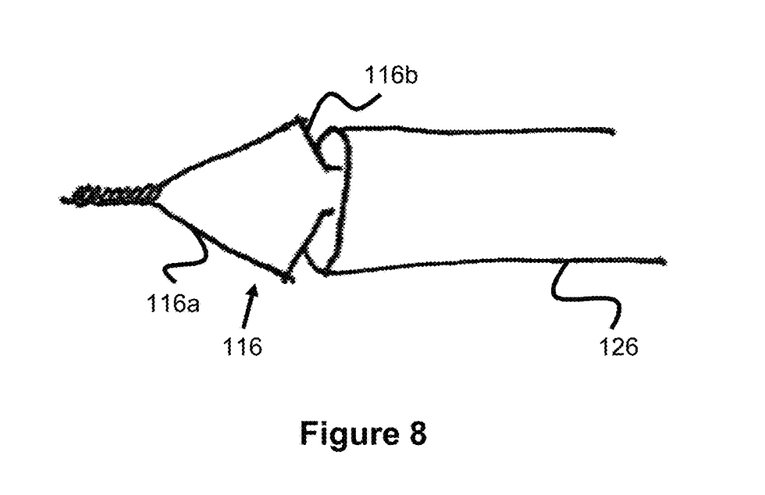
FIG. 8 illustrates a guidewire with a wedge-shaped projection according to one embodiment.

In one embodiment, guidewire projection 116 comprises a soft plastic polymer—specifically a unitary polymer piece with a hole through it which the guidewire is placed through. Alternatively, the polymer projection can be extruded over guidewire 110. Alternatively, the projection can be manufactured separately and affixed over guidewire 110 via adhesive. The projection 116 can have a number of shapes, as contemplated earlier. In particular, the shape of the sides will affect how projection 116 reacts on contact with a vessel wall. Shape examples for projection 116 include a gradual, conical shape as shown in FIG. 8 as element 116a or a concave or convex rounded shape.

In one example, the proximal 110a and distal 110b portion of guidewire 110 are manufactured separately. Projection 116 is placed over the distal portion 110b of the guidewire 110 utilizing any of the techniques described above. The distal portion 110b and proximal portion 110a of guidewire 110 are then mated together utilizing various techniques such as heat treatment, adhesive, soldering, welding, etc. In another example, guidewire 110 is manufactured as one piece and any of the techniques described above are used to place projection 116 over the distal portion of guidewire 110.

Guidewire 110 can be used with an aspiration or suction catheter, where a vacuum source is placed at the proximal end of the aspiration/suction catheter. Aspiration or suction is sometimes used to aid in clot retrieval, where said aspiration or suction is used to remove a clot lodged in the vasculature. Here, aspiration or suction could be used to seal guidewire 110 relative to the guide catheter 38. In one example, suction is used to seal guidewire projection 16 to the guide catheter 38 to seal the gap between said guidewire 110 and said guide catheter 38. The guide catheter 38 is then advanced through the vasculature while suction is applied at the proximal end of the guide catheter 38 to continue to seal the guidewire projection to the catheter.

Figure 7A:
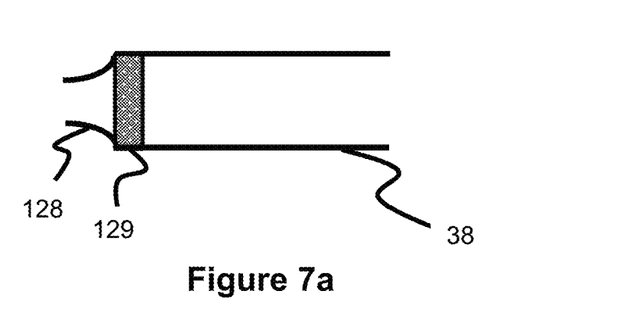
FIGS. 7a-7b illustrates a catheter with a radially reduced distal section according to one embodiment.
Figure 7B:
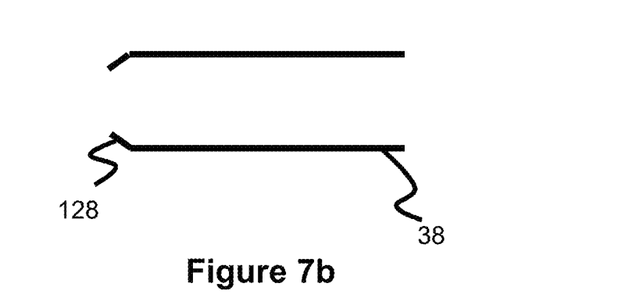

In one embodiment, the distal part of guide catheter 38 is radially smaller compared to the rest of the guide catheter. Guidewire 110 with projection 116 can be pushed through guide catheter 38, while projection 116 will contact the radially reduced distal portion of guide catheter 126 to seal the gap between guide catheter 38 and guidewire 110. A distal-tip segment 138 can be radially smaller as shown in FIG. 7a, or alternatively the distal-tip 138 can be tapered inwards in order to contact the projection as shown in FIG. 7b. In some embodiments, a marker band 129 as shown in FIG. 7a could optionally be used directly next to the radially reduced region where the guidewire projection marker band 118 would align with the guide catheter 38 radially reduced section marker band 129 so the user could confirm proper placement of guidewire 110 relative to the guide catheter 38. In another embodiment, guide catheter 38 has a relatively consistent diameter and guidewire projection 116 is malleable enough so that when the user pushes and pulls the guidewire 110, guidewire projection 116 will contract and easily pass through guide catheter 38.

In one embodiment shown in FIG. 8, guidewire projection 116 takes on a wedge-shape and has tapered distal 116a and proximal 116b surfaces. The tapered proximal surface is about the size of the guide catheter 116 diameter or slightly oversized compared to the guide catheter diameter in order to eliminate any gap between guidewire 116 and the guide catheter 38. If guidewire projection 116 is slightly oversized compared to the guide catheter 38, the guidewire projection should be malleable to enable compression to allow guidewire 110 to be tracked (pushed/pulled) through guide catheter 38 without issue.

Figure 9:
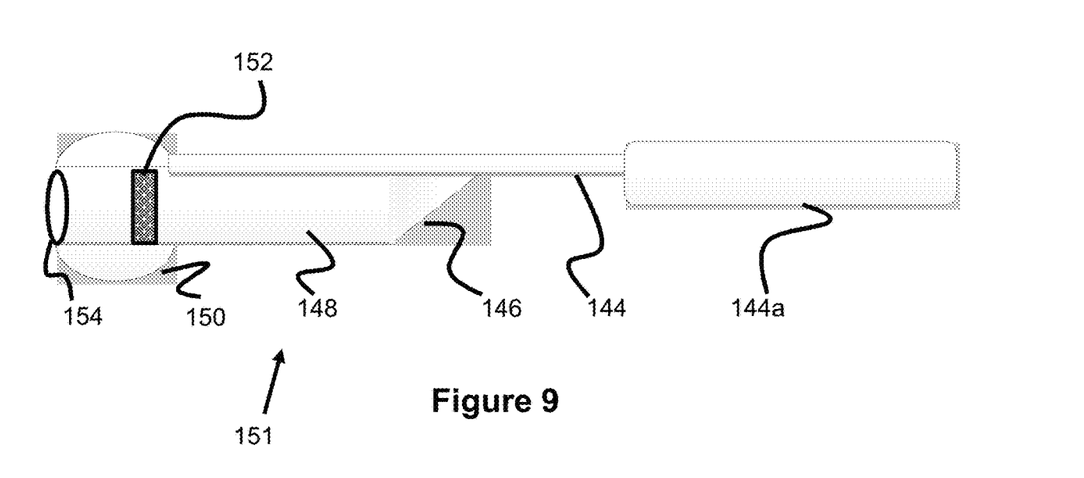
FIG. 9 illustrates a rapid exchange system to place over a guidewire according to one embodiment.

Another embodiment, shown in FIG. 9, can utilize an intermediate rapid exchange system in which an easily deployable device bridges the gap between a guidewire and the guide catheter, and said device can be tracked over the guide wire to eliminate this gap. In operation, a traditional guidewire would be used and if there is a gap between the guidewire and the overlying guide catheter and this gap is caught on a vessel bifurcation, the user can track the rapid exchange device over the guidewire to eliminate the gap. Alternatively, if the user was operating the guidewire through a bifurcation region, he or she could preemptively track the rapid exchange system over the guidewire to bridge the gap between the guidewire and guide catheter and mitigate a potential problem with the ledge effect.

FIG. 9 shows a rapid exchange intermediate catheter 151 utilizing a core wire 144 with a proximal handle 144a that the user uses to manipulate (e.g. push and pull) the catheter 151. The distal portion of the core wire 144 connects to a tubular portion 148 that has a proximal opening 146 and a distal opening 154 to allow passage of the guidewire 22. Tubular portion 148 can optionally use a radiopaque marker band 152. Guide catheters typically include a marker band at a point 3 centimeters from the distal tip, so the tubular portion's marker band 152 can be used to ensure proper alignment with the distal tip of the guide catheter. The distal portion of tubular portion 148 includes a bulbous or enlarged region 150 that bridges the gap between the tubular portion 148 and the interior of the guide catheter 38. Region 150 is navigated to the distal tip of the guide catheter 38 such that the gap between the core wire 144 and the distal opening of the guide catheter 38 is eliminated. In practice, if the user wants to eliminate the guide catheter distal tip gap between a guidewire already deployed within a guide catheter and the guide catheter, the user would track tubular portion 148 of the rapid exchange system over the guidewire, pushing the system via core wire 144 until the system is appropriately placed such that enlarged region 150 fills the gap between the guide catheter and the guide wire.

Please note figures offered are provided as illustrative visual examples helped in interpretation; sizes and measurements are only offered as illustrative examples and not meant to be specifically limited to what is literally cited.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A microcatheter used to navigate through a blood vessel bifurcation region for addressing a ledge effect, comprising:
    a microcatheter body having a guidewire passage therethrough;
    a bulb having an enlarged outer diameter relative to a proximal portion of the microcatheter body; the bulb being comprised of a polymeric material;
    wherein, in a delivery configuration, the bulb of the microcatheter is located within a lumen of a guide catheter, wherein the lumen has an inner diameter being at most about 0.003 inches greater than the enlarged outer diameter of the bulb; and,
    a distal tip distal to the bulb and having an outer diameter smaller than the enlarged outer diameter of the bulb.

2. The microcatheter of claim 1, wherein the bulb is comprised entirely of the polymeric material.

3. The microcatheter of claim 2, wherein the polymeric material has a Shore Hardness between 10A and 72D.

4. The microcatheter of claim 1, further comprising a first marker band located at a proximal portion of the bulb and a second marker band located at a distal portion of the bulb.

5. The microcatheter of claim 4, further comprising a third marker band located on the distal tip.

6. The microcatheter of claim 1, wherein the distal tip has a constant outer diameter.

7. The microcatheter of claim 1, wherein the proximal portion of the microcatheter body has an outer diameter that is larger than the distal tip outer diameter.

8. The microcatheter of claim 1, wherein the microcatheter body has a length within an inclusive range of about 148-168 cm.

9. The microcatheter of claim 1, wherein the guidewire passage has a diameter of about 0.021 inch.

10. The microcatheter of claim 1, wherein the bulb has an outer diameter of about 0.67 inches.

11. The microcatheter of claim 1, wherein the microcatheter body has a length within an inclusive range of about 148-168 centimeters, the bulb has a length within an inclusive range of about 0.5-3 centimeters, and an outer diameter of the microcatheter is within an inclusive range of about 0.013-0.073 inches.

12. The microcatheter of claim 1, the bulb creating an interface to minimize an open space between the microcatheter and an overlying guide catheter, the interface including a gap between the microcatheter and the overlying guide catheter, and the gap being about 0.0015 inch around all sides of the microcatheter.

13. The microcatheter of claim 1, wherein the bulb is located at a distal portion of the guide catheter.

14. The microcatheter of claim 1, wherein a distal portion of the bulb extends distally from the lumen of the guide catheter.

15. The microcatheter of claim 1, further comprising a substantially uniform gap of about 0.0015 inches between the guide catheter and the outer diameter of the bulb.

16. A microcatheter used to navigate through a blood vessel bifurcation region for addressing a ledge effect, comprising:
    a microcatheter body having a guidewire passage therethrough;
    a solid, cylindrical portion formed of a polymeric material and having an enlarged outer diameter relative to a proximal portion of the microcatheter body;
    a distal tapered portion immediately adjacent to the cylindrical portion; and
    a proximal tapered portion immediately adjacent to the cylindrical portion, the proximal tapered portion being symmetrical to the distal tapered portion;
    wherein, in a delivery configuration, the cylindrical portion of the microcatheter is located within a lumen of a guide catheter, wherein the lumen has an inner diameter being at most about 0.003 inches greater than the enlarged outer diameter of the cylindrical portion; and,
    a distal tip being immediately adjacent to the distal tapered portion and having an outer diameter smaller than an outer diameter of the cylindrical portion.

17. The microcatheter of claim 16, wherein the cylindrical portion is noninflatable.

18. The microcatheter of claim 16, wherein the cylindrical portion is comprised entirely of the polymeric material.

19. The microcatheter of claim 16, wherein the microcatheter body has a length within an inclusive range of about 148-168 centimeters, the cylindrical portion has a length within an inclusive range of about 0.5-3 centimeters, and the distal tip has a length within an inclusive range of about 0.5-6 centimeters.

20. A microcatheter used to navigate through a blood vessel bifurcation region for addressing a ledge effect, comprising:
    a microcatheter body having a guidewire passage therethrough; and,
    a bulb having an enlarged outer diameter relative to a proximal portion of the microcatheter body; the bulb being composed of a noninflatable polymeric material and having a cylindrical shape with symmetrically tapered proximal and distal ends;
    the bulb creating an interface to minimize an open space between the microcatheter and an overlying guide catheter, the interface including a gap between the microcatheter and the overlying guide catheter, and the gap being about 0.0015 inch around all sides of the microcatheter.

21. The microcatheter of claim 20, wherein the bulb is composed entirely of the polymeric material.

22. The microcatheter of claim 20, wherein the microcatheter body has a length within an inclusive range of about 148-168 centimeters and an outer diameter of the microcatheter is within an inclusive range of about 0.013-0.073 inches.

23. A kit of parts used to navigate through a blood vessel bifurcation region for addressing a ledge effect by bridging a gap in a guide catheter, comprising:
- the guide catheter having an inner passage therein;
- a microcatheter sized to fit within the inner passage of the guide catheter;
- the microcatheter having a distal bulb section with an enlarged outer diameter, the distal bulb section creating an interface to minimize an open space between the microcatheter and the guide catheter, the interface including a gap between the microcatheter and the guide catheter, and the gap being about 0.0015 inch around all sides of the microcatheter.

* * * * *